(12) United States Patent
Itoh

(10) Patent No.: US 7,229,175 B2
(45) Date of Patent: Jun. 12, 2007

(54) OPHTHALMIC IMAGE SENSING APPARATUS

(75) Inventor: Hiroshi Itoh, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/335,511

(22) Filed: Jan. 20, 2006

(65) Prior Publication Data

US 2006/0132710 A1    Jun. 22, 2006

Related U.S. Application Data

(63) Continuation of application No. PCT/JP2005/013436, filed on Jul. 14, 2005.

(30) Foreign Application Priority Data

Jul. 20, 2004    (JP) .............................. 2004-211690

(51) Int. Cl.
*A61B 3/14* (2006.01)
*A61B 3/10* (2006.01)
*A61B 5/00* (2006.01)

(52) U.S. Cl. ...................... 351/206; 351/221; 600/318; 600/321

(58) Field of Classification Search ................ 351/206, 351/221, 246; 396/18; 600/309, 310, 318, 600/321
See application file for complete search history.

(56) References Cited

U.S. PATENT DOCUMENTS

| | | | | |
|---|---|---|---|---|
| 5,214,454 A | * | 5/1993 | Sano | 351/206 |
| 5,530,493 A | * | 6/1996 | Suzuki | 351/206 |
| 5,594,512 A | * | 1/1997 | Yoneda et al. | 351/206 |
| 5,894,337 A | | 4/1999 | Okinishi et al. | |
| 6,193,372 B1 | | 2/2001 | Okumura et al. | |
| 6,997,874 B2 | | 2/2006 | Itoh | |
| 2004/0090596 A1 | * | 5/2004 | Okinishi | 351/206 |
| 2004/0095554 A1 | * | 5/2004 | Ono | 351/206 |
| 2004/0189937 A1 | * | 9/2004 | Okinishi | 351/206 |
| 2005/0117116 A1 | * | 6/2005 | Murakami | 351/211 |
| 2006/0126017 A1 | * | 6/2006 | Mizuochi | 351/206 |

FOREIGN PATENT DOCUMENTS

| | | |
|---|---|---|
| JP | 4-189341 A | 7/1992 |
| JP | 7-303610 | 11/1995 |
| JP | 3056287 B2 | 4/2000 |
| JP | 2003-70746 | 3/2003 |

* cited by examiner

*Primary Examiner*—David N. Spector
(74) *Attorney, Agent, or Firm*—Fitzpatrick, Cella, Harper & Scinto

(57) ABSTRACT

An ophthalmic image sensing apparatus includes an examination optical system for examining an eye to be examined, an image sensing optical system for sensing an image of the eye to be examined, an examination image pickup element for picking up the image of the eye to be examined through the examination optical system, an image-sensing image pickup element for picking up the image of the eye to be examined through the image sensing optical system, an examination condition setting device for determining image sensing states of the examination optical system and the examination image pickup element, and a driving device for determining image sensing states of the image sensing optical system and the image-sensing image pickup element based on the examination conditions determined by the examination condition setting device.

10 Claims, 4 Drawing Sheets

| VALUE INDICATED BY KNOB 24 | VOLTAGE APPLIED ONTO LIGHT SOURCE 1 | GAIN SET BY GAIN CHANGING MEANS 20 |
|---|---|---|
| 1 | 0V | 0dB |
| 2 | 2V | 0dB |
| 3 | 4V | 0dB |
| 4 | 8V | 0dB |
| 5 | 16V | 0dB |
| 6 | 16V | 6dB |
| 7 | 16V | 12dB |
| 8 | 16V | 18dB(1bit_Shift) |
| 9 | 16V | 24dB(2bit_Shift) |

| INDICATER SET BY SWITCH 33 | VOLTAGE APPLIED ONTO CONDENSER | GAIN SET BY GAIN CHANGING MEANS 20 |
|---|---|---|
| F1 | 53V | 0dB |
| F2 | 75V | 0dB |
| F3 | 106V | 0dB |
| F4 | 150V | 0dB |
| F5 | 212V | 0dB |
| F6 | 300V | 0dB |
| F7 | 300V | 6dB |
| F8 | 300V | 12dB |

OPHTHALMIC IMAGE SENSING APPARATUS

This application is a continuation of International Application No. PCT/JP2005/013436, filed on Jul. 14, 2005, which claims the benefit of Japanese Patent Application No. 2004-211690, filed on Jul. 20, 2004.

BACKGROUND OF THE INVENTION

1. Field of the Invention

The present invention relates to an ophthalmic image sensing apparatus including an examination optical system for examining an eye to be examined and an image pickup optical system for picking up an image of the eye to be examined.

2. Related Background Art

In an eye fundus examination, a color image is acquired for diagnosis using an ophthalmic image sensing apparatus such as an eye fundus camera. When ocular circulation of blood vessels on retina and pigment epithelium of the retina are to be examined in detail because of, for example, diabetic retinopathy, visible fluorescent image sensing (hereinafter referred to as Fluo image sensing) is performed. When choroid is to be examined because of macular degeneration, near-infrared fluorescent image sensing (hereinafter referred to as ICG image sensing) is performed.

Of those image sensings, the ICG image sensing has an advantage in that a fluorescent agent is more quickly circulated, a dynamic range of a change in fluorescent intensity and a variation in time are very large.

Therefore, in order to obtain a preferable image based on a wide dynamic range of the fluorescent intensity, it is necessary that an examiner change a gain of an image pickup element according to an output signal therefrom or frequently adjust a strobe scope light intensity.

The following method has been disclosed (see Japanese Patent Application Laid-Open No. H04-189341). When an image sensing mode such as a color image sensing mode is shifted to an ICG image sensing mode, because the fluorescent intensity of the ICG is high in the early stage thereof, image sensing is performed while strobe scope emission is inhibited without any condition. In the later stage, when the examiner determines that the strobe scope emission is necessary, strobe scope image sensing is performed by the operation of a light emission inhibition releasing means.

There has been disclosed a method of detecting output values from respective pixels of an image pickup element on a scanning line and calculating a strobe scope emission intensity based on the result to control an emission intensity of an image sensing light source (see JP-B 3056287).

In the above-mentioned conventional example, when a preferable image sensing condition is to be set, the examiner requires skill to simultaneously adjust and set a strobe scope light intensity and a gain.

In the case of the control for inhibiting the strobe scope emission when the image sensing mode is shifted to the ICG image sensing mode, there is an advantage to the non-emission of strobe scope light in the early stage. However, in the later stage of the image sensing, the strobe scope light image sensing is required in the relation with the sensitivity of the image pickup element.

At this time, it is necessary to allow the strobe scope emission using the strobe scope emission releasing means by the examiner.

An image sensing condition is controlled depending only on whether the strobe scope light is emitted or not and the emission intensity.

In the method of detecting the output values from the respective pixels of the image pickup element to control the strobe scope emission intensity, the strobe scope light intensity is changed depending on a level of an observation light intensity during the examination performed by the examiner. In addition, the strobe scope light intensity is changed depending on the selection of a target scanning line on the image pickup element in some cases, so the learning of the image sensing technique is required.

SUMMARY OF THE INVENTION

The present invention has been made to solve the problem described above and has an object to provide an ophthalmic image sensing apparatus capable of changing the image sensing condition based on the examination condition.

An ophthalmic image sensing apparatus, includes: an examination optical system for examining an eye to be examined; an image sensing optical system for sensing an image of the eye to be examined; examination image pickup means for picking up the image of the eye to be examined through the examination optical system; image-sensing image pickup means for picking up the image of the eye to be examined through the image sensing optical system; examination condition setting means for determining image sensing states of the examination optical system and the examination image pickup means; and driving means for determining image sensing states of the image sensing optical system and the image-sensing image pickup means based on the examination conditions determined by the examination condition setting means.

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE PREFERRED EMBODIMENTS

Preferred embodiment(s) of the present invention will be described in detail in accordance with the accompanying drawings.

Figure 1:
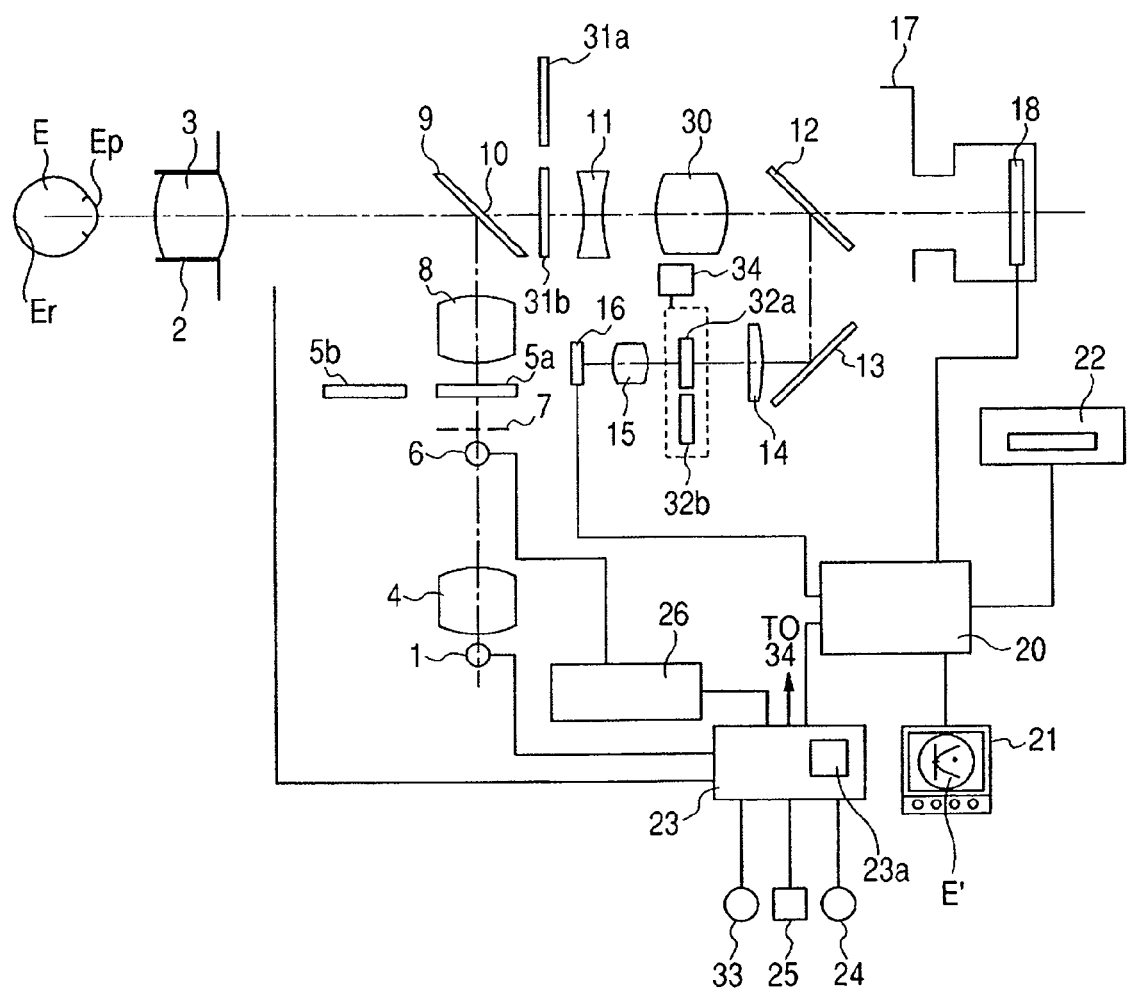
FIG. 1 is an arrangement diagram showing an ophthalmic image sensing apparatus according to an embodiment of the present invention.

The present invention will be described in detail according to the embodiment illustrated in the drawings. FIG. 1 is a structural diagram showing an eye fundus camera to which an image pickup means 18 capable of performing color image sensing and visible fluorescent image sensing is attached. A condenser lens 4, an image sensing light source 6 for emitting the flash of visible light such as a strobe scope light source, a diaphragm 7 having a ring opening, a lens 8, and a holed mirror 9, which compose a fundus illumination optical system are disposed in order on an optical path between an examination light source 1 for emitting visible light such as a halogen lamp and an objective lens 3 fixed to a lens barrel 2, and compose fundus illuminating means together with the examination light source 1. The fundus illumination optical system includes an ICG exciter filter 5a inserted to the optical path at the time of the near-infrared fluorescent image sensing, an optical path length correcting glass 5b which has the same thickness as that of the ICG exciter filter 5a and is inserted to the optical path at the time of the color image sensing, and a Fluo exciter filter (not shown) inserted to the optical path according to the image sensing mode at the time of the Fluo image sensing.

The holed mirror 9 includes an image sensing diaphragm 10 disposed in a hole portion thereof. An image sensing lens 11 movable for focusing, an imaging lens 30, and a flip-up mirror 12 are disposed on an optical path behind the image sensing diaphragm 10. A mirror 13, a field lens 14, a focal lens 15, and an image pickup element 16 sensitive to near-infrared are disposed in order on an optical path in a reflection direction of the flip-up mirror 12.

When the flip-up mirror 12 is flipped up, an image pickup means 18 with a finder, which is sensitive to a visible region is attached through a camera mount 17. The objective lens 3, the image sensing diaphragm 10, the focal lens 11, and the imaging lens 30 compose a visible fundus examination and image-sensing optical system. The mirror 13, the field lens 14, and the focal lens 15 compose a near-infrared fundus examination and image-sensing optical system.

The fundus examination and image-sensing optical systems include a Fluo barrier filter 31a inserted at the time of the fluo image sensing, an ICG image sensing barrier filter 32a, and an optical path length correcting glass 31b which has the same thickness as that of an ICG examination barrier filter 32b and is inserted to the optical path at the times of the color image sensing and the ICG image sensing. The Fluo barrier filter 31b is to be inserted to the optical path at the time of the visible fluorescent image sensing, and the ICG barrier filter 32a is to be inserted to the optical path at the time of the near-infrared fluorescent image sensing. The ICG examination barrier filter 32b is inserted at the time of the ICG examination and a transmission wavelength region thereof becomes a band slightly wider than that of the filter 32a. The optical system includes a barrier filter detecting means 34 for detecting which of the ICG barrier filter 32a and the ICG examination barrier filter 32b is located on the optical path.

Image output signals from the image pickup elements 18 and 16 are inputted to a gain changing means 20. The gain changing means 20 amplifies the image output signals according to instructions from a control portion 23 to display images on a monitor 21 or to store the images in a memory means 22.

The control portion 23 is connected with a switch 24 for setting a halogen light intensity and the gain of an image pickup element, an image sensing switch 25, an image sensing light source controlling means 26, a knob type switch 33 for inputting a strobe scope light intensity and the gain of the image pickup element 16, the filter detecting means 34, and the examination light source 1 in addition to the connection with the gain changing means 20.

The image sensing switch 25 is a switch which is pressed down when the image sensing is performed by an examiner. When the examiner recognizes that a fundus image is dark while examining an eye fundus to be examined Er, the switch 24 is used to adjust the halogen light intensity or increase the gain.

The image sensing light source controlling means 26 performs not only light intensity setting but also non-light emission control on the image sensing light source 6 based on the control of the control portion 23.

Figures 2, 3, 4:
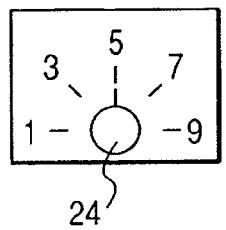
FIG. 2 is a detailed view showing a switch 24.
FIG. 3 is a table showing an applied voltage and a gain of a camera.
FIG. 4 is a table showing a charging voltage and the gain of the camera.

Next, light intensity and gain adjustments using the switch 24 will be described. The switch 24 is a knob type and marks "1" to "9" are provided around the switch 24 as shown in FIG. 2. Continuous adjustment can be made among the marks. An angle of the knob is detected by a known angle detecting means. Detection information is sent to the control portion 23. The control portion 23 controls a voltage applied onto the examination light source 1 and a gain set by the gain changing means 20 based on a table shown in FIG. 3. That is, when the switch 24 indicates a value corresponding to the mark "3", the voltage applied onto the examination light source 1 is 4 V and the gain set by the gain changing means 20 is 0 dB. When the switch 24 indicates a value corresponding to the mark "5", the voltage applied onto the examination light source 1 is 16 V and the gain set by the gain changing means 20 is 0 dB. When the switch 24 indicates a value corresponding to the mark "7", the voltage applied onto the examination light source 1 is 16 V and the gain set by the gain changing means 20 is 12 dB. When a value corresponding to the mark "9" is indicated, the voltage applied onto the examination light source 1 is 16 V and the gain set by the gain changing means 20 is 24 dB (2-bit shift). The bit shift used in this embodiment is an amplification method of processing an electrical signal from the image pickup element 16 by the gain changing means 20 to display a pseudo bright image with reduced resolution. A 1-bit shift reduces the resolution by 1 bit and a 2-bit shift reduces the resolution by 2 bits, so the quality of an output image is inferior to that of an image which is not subjected to the bit shift.

When a position indicated by the switch 24 is located between the marks, a value according to a positional ratio is set. The voltage and the gain are instantly changed, so a person who performs image sensing can adjust the brightness of the fundus image in a wide dynamic range while watching the monitor 21.

As described above, while the switch 24 is adjusted to examine the fundus of an eye to be examined with suitable brightness, the alignment with the eye to be examined, the focusing with movement of the focal lens 3, and the checking of an image sensing area are performed using an operation means (not shown).

Next, light intensity and gain adjustments using the switch 33 will be described. When the switch 33 is operated, a value changes stepwise from F1 to F8. The value set by the switch 33 is detected by the control portion 23. The control portion 23 sets a charge voltage applied onto a condenser of the image sensing light source controlling means 26 and the gain set by the gain changing means 20 based on a table shown in FIG. 4. Note that a signal gain at this time is set in response to the input of the image sensing switch 25 as described later.

In other words, when detecting that the value set by the switch 33 is F1, the control portion 23 sets the voltage applied onto the condenser included in the image sensing light source controlling means 26 to 53 V and causes a memory 23a to store the gain set by the gain changing means 20 which is 0 dB. Similarly, when detecting that the value set by the switch 33 is F7, the control portion 23 sets the voltage applied onto the condenser to 300 V and causes the memory 23a to store the gain set by the gain changing means 20 which is 6 dB.

In the case of the color image sensing, the optical path length correcting glass 5b is inserted to the fundus illumination optical system and the optical path length correcting glass 31b is inserted to the fundus examination and image-sensing optical systems. The flip-up mirror 12 is moved to the outside of the optical path. A reflectance of the fundus to visible light is high, so an adjustable range of the switch 24 is limited to 1 to 5. That is, the gain is not changed. When the input of the image sensing switch 25 is detected, the control portion 23 starts light accumulation of the image pickup element 18 and sends an emission signal to the image sensing light source controlling means 26. When the emission signal is received, the image sensing light source 6 emits light based on charges accumulated in the condenser included in the image sensing light source controlling means 26. A light flux emitted from the image sensing light source 6 passes through the opening of the diaphragm 7 having the ring opening as in the examination light. Visible light passes through the lens 8 and is reflected on a mirror portion located in the periphery of the holed mirror 9 leftward. Reflected light passes through the objective lens 2 and the eye fundus Er is illuminated with the reflected light through an eye pupil to be examined Ep. An image of the fundus illuminated thus passes through the objective lens 2, the image sensing diaphragm 10, the focal lens 11, and the imaging lens 30. The image is formed on the image pickup element 18 and converted into an electrical signal. The gain changing means 20 does not amplify the signal and causes the memory means 22 to store the sensed image. In addition to this, the fundus image is displayed on the monitor 21.

Next, the case of the ICG image sensing will be described. First, as in the case of the color image sensing, a pupil dilating agent is applied to a person to be examined and the person whose pupil is dilated is seated facing the objective lens 2. Then, the ICG exciter filter 5a and the ICG examination barrier filter 32b are inserted onto the optical path.

In such a structure, light emitted from the examination light source 1 travels on the same optical path as that described above and the fundus is illuminated with only near-infrared light through the ICG exciter filter 5a. An image of the fundus illuminated thus travels on the same optical path as that described above and is flipped by the flip-up mirror 12. The image is formed on the image pickup element 16 through the ICG examination barrier filter 32b and converted into an electrical signal. The electrical signal is inputted to the gain changing means 20 and amplified by a predetermined gain. The signal is displayed on the monitor 21. As described above, the ICG examination barrier filter 32b has a wide transmission wavelength region. Therefore, even when fluorescence is not caused, it is possible to examine a state of the fundus. The examiner examines the fundus image displayed on the monitor 21 and operates the switch 24 so as to obtain a brightness at which it is easy to watch the fundus image of the eye to be examined. After the examiner watches the fundus image displayed on the monitor and checks that the alignment and the focusing are preferable, a fluorescent agent is injected to the person to be examined. In addition to this, a timer is started and the ICG image sensing barrier filter 32a is inserted onto the optical path. The examiner operates the switch 24 to set the value to, for example, about 9, so the intensity of light emitted from the examination light source 1 increases and the gain set by the gain changing means 20 rises. Therefore, appearance of a fluorescent image which is weak light is awaited. When the fluorescent image appears, the image sensing switch 25 is operated.

Here, the case of the ICG image sensing as an example by which this embodiment is most characterized will be described in detail with reference to a flow chart shown in FIG. 5.

When the examiner selects an ICG image sensing mode to perform image sensing, the ICG exciter filter 5a is automatically inserted into the fundus illumination optical system and the ICG examination barrier filter 32b is automatically inserted into the fundus examination and image-sensing optical system (Step 1).

In Step 2, the examiner performs alignment and focusing while examining the eye to be examined which is displayed on the monitor 21. The ICG examination barrier filter 32b is inserted as the batter filter in Step 1. Note that, even when the image sensing barrier filter is used in the early stage of the ICG image sensing, sufficient examination is possible. Therefore, it is also possible to change the barrier filter to the ICG image sensing barrier filter 32a by the operation of the examiner.

At this time, the knob 24 is turned such that the eye fundus Er can be precisely examined, so a halogen light intensity and a gain of an output signal from the image sensing element 16 are adjusted. The adjustment made by the knob 24 has been described with reference to FIGS. 2 and 3.

In Step 3, as was described with reference to FIG. 4, the examiner turns the switch 33 to adjust the strobe scope light intensity and the gain.

In Step 4, the examiner turns on the image sensing switch 25 to perform image sensing.

In Step 5, when an image sensing start signal is inputted to the control portion 23, the control portion 23 detects whether or not the ICG image sensing barrier filter 32a is inserted based on an output from the barrier filter detecting means 34. Subsequent processing depends on the result obtained by detection. When the ICG examination barrier filter 32b is inserted, processing goes to Step 9 and the control portion 23 replaces the ICG examination barrier filter 32b with the ICG image sensing barrier filter 32a. Then, in Step 10, the strobe scope light intensity and the gain which are set by the examiner in Step 3 are detected and the charge voltage applied onto the condenser of the image sensing light source controlling means 26 and the gain set by the gain changing means 20 are set to the values stored in the memory 23a. As is apparent from FIG. 4, the gain set at this time is set to a gain lower than the gain predetermined in the control portion in Step 6. After the completion of setting, in Step 11, the image sensing light source 6 emits light and the image of the eye fundus to be examined Er is picked up by the image pickup means 16.

On the other hand, when it is detected in Step 5 that the ICG image sensing barrier filter 32a is inserted, in Step 6, the control portion 23 reads out the halogen light intensity and a set value of the gain of the output signal from the image sensing element 16, which were adjusted by the examiner in Step 2. Then, the read result is compared with the gain (18 dB is assumed here) predetermined in the control portion 23. As shown in FIG. 3, when the value set by the knob 24 is equal to or larger than 8, processing moves to Step 10 and subsequent processing is identical to the above-mentioned processing.

When the value set by the knob 24 is smaller than 8 in Step 6, the control portion 23 can determine that there is no case where a fluorescent image is deteriorated even when the image is sensed in the fluorescent image sensing. Therefore, it is possible to allow the light accumulation of the image pickup element 16 with illumination light from the examination light source 1 without using the image sensing light source 6.

Therefore, in Step 7, the condenser of the image sensing light source controlling means 26 is not changed or the output of the strobe scope emission signal from the control portion 23 is disabled. When the gain is set (value set by the knob 24 is smaller than 6 to 8) at the time of examination, the gain is set to the image sensing element 16.

In Step 8, the image of the eye fundus to be examined Er is sensed without the strobe scope emission.

In general, a state for several minutes after the fluorescent image starts to appear in the ICG image sensing is a state in which the fluorescent image can be examined using the ICG image sensing barrier filter 32a and image sensing can be performed without deteriorating the image even in the case of non-strobe scope emission. After that, it is hard to examine the fluorescent image because of a reduction in fluorescent light intensity. Therefore, the ICG image sensing barrier filter 32a is removed from the optical path and the ICG examination barrier filter 32b is inserted thereto to perform the examination using the bit shift. In the time of the image sensing, the barrier filter is changed into the ICG image sensing barrier filter 32a and strobe scope image sensing is performed.

The knob 24 is set by the examiner in Step 2. However, when it is assumed that the examiner neglects the setting of the knob 24 regardless of a state in which the fluorescent image cannot be examined because the fluorescent light intensity is low and thus the value set by the knob 24 is smaller than 8, the strobe scope emission is not performed. As a result, the image is likely to be very dark. Therefore, in Step 7, in addition to the controls of the image sensing light source controlling means 26 and the image pickup element 16, it is expected to employ a structure in which an output signal detecting means for detecting an output signal from the image pickup element 16 during, for example, examination is provided, a threshold of the output signal is set in the control portion 23, and an alarm is given when the output signal does not exceed the threshold.

Figure 6:
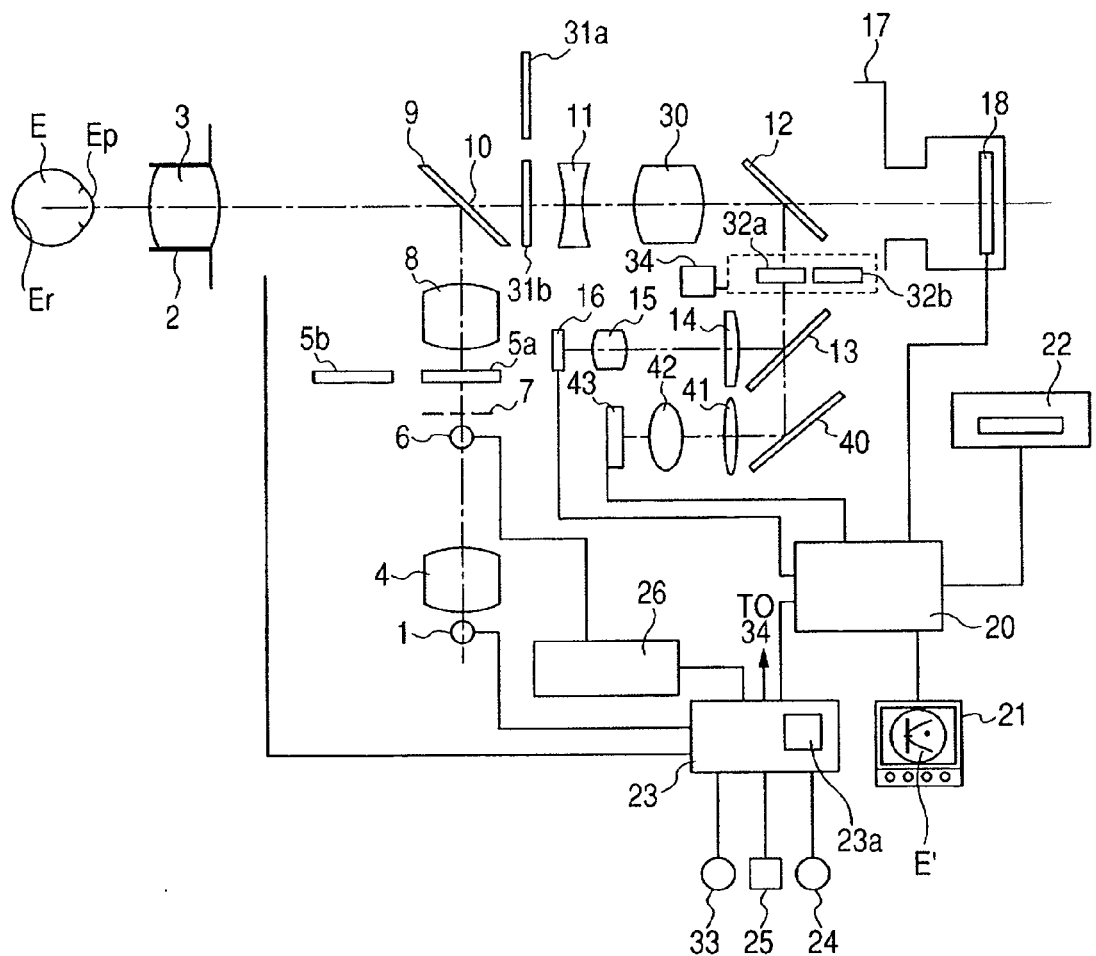
FIG. 6 is a diagram showing an embodiment in the case where an image pickup element for examination and an image pickup element for image sensing are provided.

In this embodiment, the example in which the examination and the image sensing are performed by a single image pickup element 16 is described. As shown in FIG. 6, it is also possible to provide an image pickup element for examination and an image pickup element for image sensing.

Only differences from FIG. 1 will be described. With respect to the ICG image sensing, the examination optical system extends from the objective lens 3 to the image pickup element 16 through the image sensing diaphragm 10, the flip-up mirror 12, and the mirror 13. The image sensing optical system extends from the mirror 13 to an image-sensing image pickup element 43 through a mirror 40. The mirror 13 is a movable type and located on the optical path during the examination but removed from the optical path during the image sensing.

Reference numerals 41 and 42 denote a field lens and a focal lens, respectively.

The gain set by the switch 33 described with reference to FIG. 4 (Step 3 in FIG. 5) is used for the image-sensing image pickup element 43.

Figure 5:
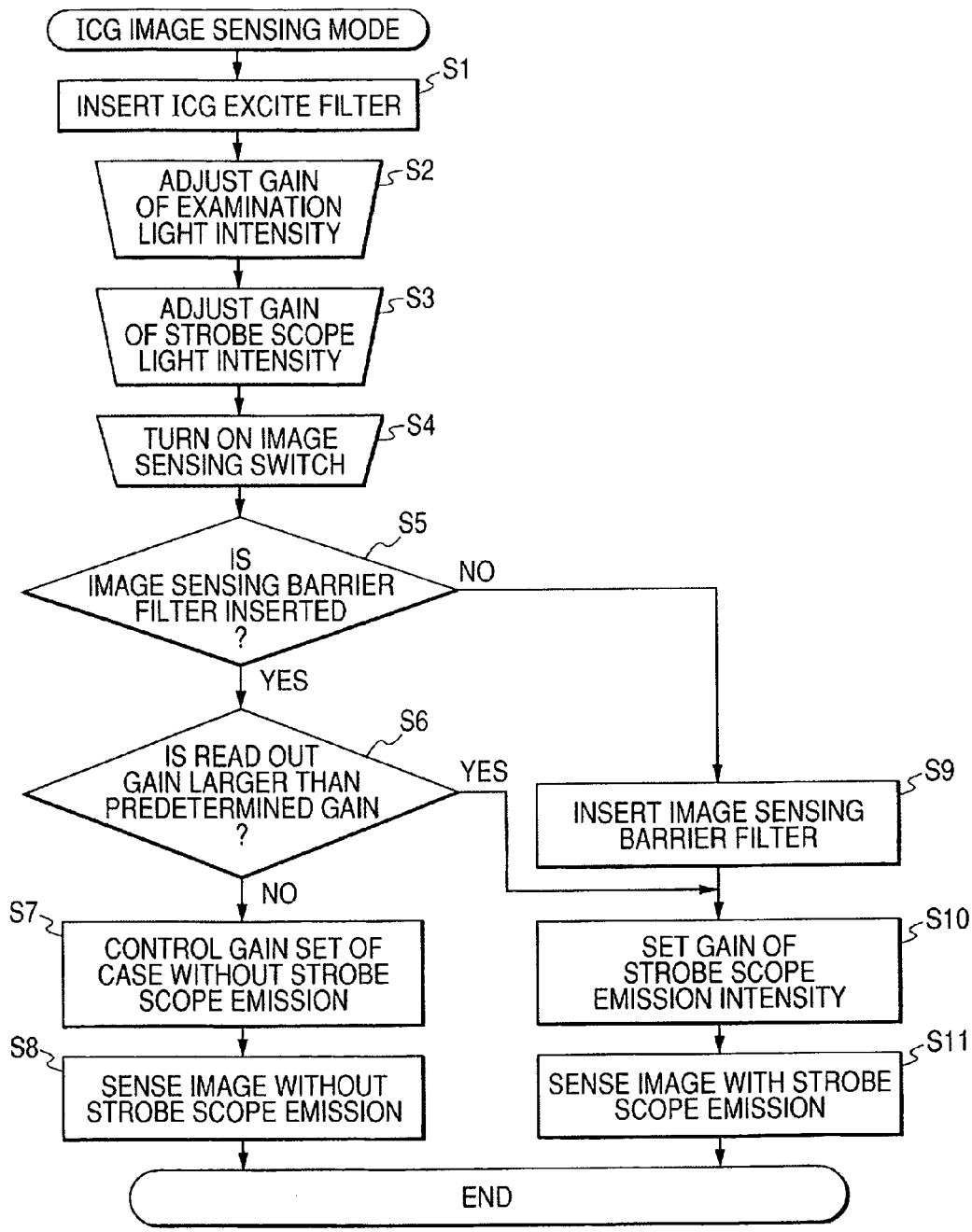
FIG. 5 is a flow chart of the embodiment according to the present invention.

The gain in Step 10 of the flow chart shown in FIG. 5 is set to the image-sensing element 43. A point of difference of this embodiment is that image sensing is performed by the image-sensing image pickup element 43 in Step 11; otherwise, operation of the apparatus in this embodiment is the same as in the forgoing description.

In this embodiment, whether or not the strobe scope light source 6 is turned on to emit light at the time of image sensing is determined using the gain set to the examination image pickup element 16 as an examination condition for determination. However, the following is expected. For example, assume that a voltage applied onto the examination light source 1, which is predetermined in the control portion 23 is set to, for example, "3" by the switch 24 in FIG. 3. When the light intensity of the examination light source 1 during the examination (that is, the applied voltage onto the examination light source 1) is higher than the voltage set to "3", the intensity of the fluorescent light from the eye to be examined is small. Therefore, when the image sensing is to be performed using the image-sensing image pickup element 43, the strobe scope light source 6 is turned on to emit light. On the other hand, when it is lower than the voltage set to "3", the image sensing using the image-sensing image pickup element 43 is performed without the light emission of the strobe scope light source 6.

In the flow chart of FIG. 5, the determination standard in Step 6 becomes "Is the value equal to or larger than the predetermined applied voltage?"

The following is also expected. When it is determined that the ICG image sensing barrier filter 32a is not located on the optical path based on the output from the barrier filter detecting means 34, the intensity of the fluorescent light from the eye to be examined is small. Therefore, when the image sensing is to be performed using the image-sensing image pickup element 43, the strobe scope light source 6 is turned on to emit light. On the other hand, when the ICG image sensing barrier filter 32a is inserted onto the optical path, the intensity of the fluorescent light from the eye to be examined is large. Therefore, the image sensing using the image-sensing image pickup element 43 is performed without the light emission of the strobe scope light source 6.

At this time, Step 6 is skipped in the flow chart of FIG. 5.

As described above, according to the ophthalmic image sensing apparatus in the above-mentioned embodiment, the control for obtaining the sensed image is changed based on the examination condition. Therefore, it is possible to perform different controls including the light emission and the non-light emission of the image sensing light source.

Assume that the examination condition is the gain set to the examination image pickup means. Therefore, when the gain is high, the image sensing can be performed while a noise component is reduced.

Assume that the examination condition is the voltage applied onto the examination light source. Therefore, when the applied voltage is high, the image sensing can be performed using the image sensing light source. When the applied voltage is low, the image sensing can be performed using only the examination light source. Thus, it is possible to lengthen the life of the image sensing light source.

The near-infrared fluorescent image sensing exciter filter is provided in the illumination optical system. The near-infrared fluorescent image sensing barrier filter is provided in each of the examination optical system and the image sensing optical system. Here, the examination condition is whether or not the near-infrared fluorescent image sensing exciter filter and the near-infrared fluorescent image sensing barrier filter are located on the optical path. When the near-infrared fluorescent image sensing barrier filters are located on the optical path, the intensity of light reflected on the eye to be examined is sufficient. Therefore, the image sensing can be performed using only the examination light source. Thus, when the barrier filters are not located on the optical path, the image sensing is performed using the image sensing light source, so the light sources can be switched.

When an examination condition is lower than the examination condition set in the control portion, the image sensing using the examination light source and the examination image pickup means is performed without the light emission of the image sensing light source. When the examination condition is high, the image sensing using the image-sensing image pickup means is performed while the image sensing light source is turned on to emit light. Therefore, it is possible to lengthen the life of the image sensing light source and the person to be examined has no uncomfortable feeling.

When the near-infrared fluorescent image sensing exciter filter and the near-infrared fluorescent image sensing barrier filter are located on the optical path, the image sensing using the examination light source and the examination image pickup means is performed without the light emission of the image sensing light source. When they are not inserted, the image sensing using the image-sensing image pickup means is performed while the image sensing light source is turned on to emit light. When the near-infrared fluorescent image sensing barrier filters are located on the optical path, the intensity of light reflected on the eye to be examined is sufficient. Therefore, the image sensing can be performed using only the examination light source. Thus, when the barrier filters are not located on the optical path, the image sensing is performed using the image sensing light source, so the light sources can be switched.

The examination image pickup means and the image-sensing image pickup means are the same image pickup means. Therefore, it is possible to reduce a size of the apparatus and a cost thereof.

When the gain is set to the examination image pickup means by a gain inputting means, the applied voltage onto the examination light source is fixed, so the inputted gain becomes independent of the examination light intensity. Therefore, the control based on the inputted gain and the predetermined gain can be performed with high precision.

According to the different controls for obtaining the sensed image, when the gain inputted by the gain inputting means is lower than the gain predetermined in the control portion, the image sensing light source is not turned on. When the gain is high, a gain of the image pickup means is changed into a gain lower than the gain set in the control portion by the gain changing means and the light emission is performed for image sensing. Therefore, when a fluorescent intensity is high, the light emission of the image sensing light source is omitted, so that it is possible to lengthen the life of the image sensing light source. The irradiation of the person to be examined with discontinuous light (strobe scope light) is omitted, so there is no uncomfortable feeling and it is possible to obtain an image having a low noise component and higher quality.

The control portion for controlling the entire system performs the different controls for obtaining the sensed image based on the gain inputted by the gain inputting means and the gain predetermined in the control portion. Therefore, in the case where sufficient diagnosis is possible even when the image sensing light source is not turned on and in the case where it is impossible, different controls including light emission and non-light emission of the image sensing light source can be performed. Whether or not the image sensing light source is turned on is determined according to the gain, so it is unnecessary to perform a non-light emission releasing operation by the examiner. Thus, the determination based an output signal related to a specific region of the eye fundus to be examined, which is picked up by the image pickup element is not performed, so the failure of image sensing is eliminated.

It is unnecessary to switch between the strobe scope emission and the non-strobe scope emission, so the operability is improved.

When the gain inputted by the gain inputting means is lower than the gain predetermined in the control portion, the image sensing light source is not turned on. When the gain is high, a gain of the image pickup means is changed into a gain lower than the gain set in the control portion by the gain changing means and the light emission is performed for image sensing. Therefore, when a fluorescent intensity is high, the light emission of the image sensing light source is omitted, so that it is possible to lengthen the life of the image sensing light source. The irradiation of the person to be examined with discontinuous light (strobe scope light) is omitted, so there is no uncomfortable feeling. When the image sensing light source is turned on to emit light, the gain increases, so it is possible to obtain an image having higher quality.

The near-infrared fluorescent image sensing exciter filter is provided in the illumination optical system. The near-infrared fluorescent image sensing barrier filter is provided in each of the examination optical system and the image sensing optical system. When the near-infrared fluorescent image sensing exciter filter and the near-infrared fluorescent image sensing barrier filters are inserted onto the optical path, different controls are performed during the image sensing. Therefore, it is unnecessary to charge the image sensing light source, so an image sensing interval can be shortened when continuous image sensing is performed in the early stage of the near-infrared fluorescent image sensing. Thus, a change in ocular circulation with time can be diagnosed in detail.

When the gain is set to the examination image pickup means by the gain inputting means, the applied voltage onto the examination light source is fixed. Therefore, the inputted gain becomes independent of the examination light intensity, so the control based on the inputted gain and the predetermined gain can be performed with high precision.

When the near-infrared fluorescent image sensing barrier filters are not inserted onto the optical path during examination, the fluorescent intensity has already been low. Therefore, the control unit causes the image sensing light source to be turned on regardless of the gain inputted from the gain inputting means, so it is possible to obtain a high quality image.

A moving image is obtained during examination and image sensing and a still image is obtained as the sensed image, so it is easy to examine during examination. Therefore, an image having a low noise component and higher quality can be obtained as compared with the examined image.

The signal detecting means for detecting the output signal from the image pickup element while the eye is examined using the image pickup element is provided and an output signal threshold is set in the control portion. When the output signal is lower than the output signal threshold and the gain inputted by the gain inputting means is lower than the predetermined gain, the control portion gives an alarm. Therefore, when the gain is set to a low value by the examiner regardless of a state in which the fluorescent light intensity is low and the fluorescent image cannot be examined, the strobe scope emission is not performed. Thus, the failure of image sensing is eliminated.

As described above, according to the present invention, an ophthalmic image sensing apparatus capable of changing the image sensing condition based on the examination condition is provided.

This application claims priority from Japanese Patent Application No. 2004-211690 filed Jul. 20, 2004 which is hereby incorporated by reference herein.

What is claimed is:

1. An ophthalmic image sensing apparatus, comprising:
   a first image pickup device for picking up an image of an eye to be examined with a monitor;
   a second image pickup device for picking up an image of the eye to be stored, after the image of the eye is picked up by the first image pickup device;
   a light source for illuminating the eye when the image of the eye is picked up by the second image pickup device;
   an examination condition setting switch for setting an examination condition on the monitor to adjust a brightness of a fundus image being picked up by the first image pickup device; and
   a controller for determining whether or not to illuminate the eye by the light source based on the examination condition set by the examination condition setting switch, when the image of the eye is picked up by the second image pickup device.

2. An ophthalmic image sensing apparatus according to claim 1, wherein the examination condition is a gain of an image output signal from the first image pickup device.

3. An ophthalmic image sensing apparatus according to claim 1, further comprising:
   an examination light source for illuminating the eye the image of which is to be picked up by the first image pickup device,
   wherein the examination condition is a voltage applied onto the examination light source.

4. An ophthalmic image sensing apparatus according to claim 1, further comprising:
   a near-infrared fluorescent image sensing barrier filter,
   wherein the examination condition is whether or not the near-infrared fluorescent image sensing barrier filter is located on an optical path to the first image pickup device.

5. An ophthalmic image sensing apparatus according to claim 1, wherein the first image pickup device and the second image pickup device are the same device.

6. An ophthalmic image sensing apparatus according to claim 1, further comprising:
   an examination light source for illuminating the eye the image of which is to be picked up by the first image pickup device,
   wherein, when a gain of an image output signal from the first image pickup device is set by the examination condition setting switch, an applied voltage onto the examination light source is fixed.

7. An ophthalmic image sensing apparatus according to claim 1, wherein, if a gain of an image output signal from the first image pickup device set by the examination condition setting switch is lower than a predetermined value, light emission from the light source is inhibited by the controller.

8. An ophthalmic image sensing apparatus according to claim 5, wherein, when a gain of an image output signal from the image pickup device set by the examination condition setting switch is higher than a predetermined value, a gain of the image output signal is changed to a value lower than a set gain and the light source is turned on to perform the image pickup.

9. An ophthalmic image sensing apparatus according to claim 3, wherein, if a voltage applied onto the examination light source is lower than a predetermined value, the light emission from the light source is inhibited by the controller.

10. An ophthalmic image sensing apparatus, comprising:
    a first image pickup device for picking up an image of an eye to be examined with a monitor;
    a second image pickup device for picking up an image of the eye to be stored, after the image of the eye is picked up by the first image pickup device;
    a light source for illuminating the eye when the image of the eye is picked up by the second image pickup device;
    an examination condition setting switch for setting an examination condition on the monitor to adjust brightness of a fundus image being picked up by the first image pickup device; and
    a controller for determining an emission intensity of light to illuminate the eye by the light source based on the examination condition set by the examination condition setting switch, when the image of the eye is picked up by the second image pickup device.

* * * * *

UNITED STATES PATENT AND TRADEMARK OFFICE
CERTIFICATE OF CORRECTION

PATENT NO. : 7,229,175 B2
APPLICATION NO. : 11/335511
DATED : June 12, 2007
INVENTOR(S) : Hiroshi Itoh It is certified that error appears in the above-identified patent and that said Letters Patent is hereby corrected as shown below:

ON THE TITLE PAGE
At Item (75), "Hiroshi Itoh, Tochigi (JP)" should read --Hiroshi Itoh, Utsunomiya (JP)--.

IN THE DRAWINGS
Sheet 2, Fig. 4, "INDICATER" should read --INDICATOR--.

COLUMN 1
Line 7, "2004-211690." should read --2004-211690--.

COLUMN 2
Line 19, "apparatus," should read --apparatus--.

COLUMN 3
Line 26, "region" should read --region,--.
Line 38, "times" should read --time--.

COLUMN 6
Line 17, "batter" should read --barrier--.

COLUMN 9
Line 55, "performs the" should read --performs--.
Line 66, "based an" should read --based on an--.

COLUMN 10
Line 1, "element" should read --element,--.

Signed and Sealed this

Sixth Day of May, 2008

JON W. DUDAS
*Director of the United States Patent and Trademark Office*